United States Patent
Zhang et al.

(10) Patent No.: US 9,824,148 B2
(45) Date of Patent: Nov. 21, 2017

(54) METHOD AND DEVICE FOR SEARCHING AND DISPLAYING SCATTERED LOGS

(71) Applicant: GE MEDICAL SYSTEMS GLOBAL TECHNOLOGY COMPANY, LLC, Waukesha, WI (US)

(72) Inventors: Maoquan Zhang, ChengDu (CN); Weiguo Tang, ChengDu (CN); Xueli Wang, Beijing (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 372 days.

(21) Appl. No.: 14/136,762

(22) Filed: Dec. 20, 2013

(65) Prior Publication Data

US 2014/0188860 A1    Jul. 3, 2014

(30) Foreign Application Priority Data

Dec. 28, 2012   (CN) .......................... 2012 1 0582936

(51) Int. Cl.
*G06F 17/30* (2006.01)
*G06F 19/00* (2011.01)
*G06F 11/32* (2006.01)

(52) U.S. Cl.
CPC .... *G06F 17/30864* (2013.01); *G06F 19/3412* (2013.01); *G06F 11/323* (2013.01)

(58) Field of Classification Search
None
See application file for complete search history.

(56) References Cited

U.S. PATENT DOCUMENTS

| 6,603,494 | B1 * | 8/2003 | Banks | .................... A61B 5/055 |
| | | | | 600/410 |
| 6,609,217 | B1 * | 8/2003 | Bonissone | .......... G06F 11/2257 |
| | | | | 714/26 |
| 2002/0129363 | A1 * | 9/2002 | McGuire | ................ H04H 60/33 |
| | | | | 725/37 |

(Continued)

OTHER PUBLICATIONS

Lou et al., "Automated Event Log File Recovery Based on Content Characters and Internal Structure", the 1st International Conference on Information Science and Engineering (ICISE2009), IEEE Computer Society, pp. 4778-4781, 2009.

(Continued)

*Primary Examiner* — Christopher J Raab

(57) ABSTRACT

A method for searching and displaying scattered logs, comprising: finding out one or more corresponding log data based on a search key word; determining a desired timestamp from the log data, and regarding the log data containing the timestamp as target data; searching a semantic file for related semantic data based on the search key word, and finding out related log data based on the related semantic data; time filtering the related log data to obtain filtered log data; establishing a coordinate system by mapping the target data and the filtered log data onto mapping points of the coordinate system; semantically linking the filtered log data, and dying the filtered log data and the target data; and counting the number of lines related to the target data and the filtered log data, and generating links thereto. The present invention further discloses a device for searching and displaying scattered logs.

20 Claims, 4 Drawing Sheets

(56) References Cited

U.S. PATENT DOCUMENTS

| | | | |
|---|---|---|---|
| 2004/0172307 A1* | 9/2004 | Gruber | G06Q 50/24 |
| | | | 705/3 |
| 2006/0123340 A1* | 6/2006 | Bailey | G06F 9/44526 |
| | | | 715/700 |
| 2008/0082477 A1* | 4/2008 | Dominowska | G06F 17/30616 |
| 2009/0043825 A1* | 2/2009 | Bourne | G06F 17/301 |
| 2012/0117113 A1* | 5/2012 | Fujisawa | G06F 17/30144 |
| | | | 707/771 |
| 2012/0143859 A1* | 6/2012 | Lymperopoulos | G06F 17/3087 |
| | | | 707/724 |
| 2012/0197934 A1* | 8/2012 | Zhang | G06F 17/30516 |
| | | | 707/770 |

OTHER PUBLICATIONS

Jayathilake, "A Novel Mind Map Based Approach for Log Data Extraction", 2011 6th International Conference on Industrial and Information Systems, ICIIS 2011, IEEE, pp. 130-135, Aug. 16-19, 2011.

Jayathilake, "Towards Structured Log Analysis", 2012 Ninth International Joint Conference on Computer Science and Software Engineering (JCSSE), IEEE, pp. 259-264, 2012.

* cited by examiner

METHOD AND DEVICE FOR SEARCHING AND DISPLAYING SCATTERED LOGS

TECHNICAL FIELD

Embodiments of the present invention relate to medical imaging, and in particular to a method and device for searching and displaying scattered logs.

BACKGROUND TECHNOLOGY

A log file, a special file or a collection of special files to record operational events of a computer system, mainly records every incident happening to the computer system, including startup, running and shutdown of various services. The log file includes an application program part, a security part and a system part, etc. A log file is created for the purpose of tracking a system or a user's behavior, and fast troubleshooting and solution determination.

One scan or one examination, which is referred to in the field of medical imaging, means a scan on a patient using a medical imaging device (for example, a CT device, a MRI device) to generate an image desired by a physician. This scan or examination process is completed with a plurality of scanning elements, which correspond to different subsystems, each having a unique way to maintain its log files. These subsystems that cooperate to complete a scan are referred to as an imaging chain. The tasks of respective subsystems are recorded in log files, forming semantics of their own.

Log file analysis is rather trivial and time consuming. A large amount of information is hidden in the log files, which are then scattered among various subsystems. Moreover, the relationship among these log files is so complicated that ordinary technicians would find it hard to collect desired information from these related log files, not to mention analyze these log files for troubleshooting. The information hidden in the log files is significant, but there have not yet been a simple and accurate method to read this information. Although some log analysis systems have been proposed in the art, they generally demand operations of skilled engineers of specific fields and expertise. This undoubtedly causes high cost and difficulty to the use and operation of the system.

Additionally, log files are conventionally searched and analyzed based on syntax and format, that is, log files are simply analyzed by examining whether or not they include the search keyword. That is, the existing technology fails to interpret the semantic of every item of information itself, not to mention the relationship among log files based on the semantics thereof. Consequently, when awaiting a log file analysis result, a user is only given a large amount of discrete data, which has hardly any relationship. Besides, the result is not presented via a clear and simple interface, and thus hard to read, only to increase difficulty in troubleshooting, analysis and resolution.

Therefore, there exists a need in the art for a method and device for addressing the foregoing problems.

SUMMARY OF THE INVENTION

According to one embodiment of the present invention, a method for searching and displaying scattered logs is proposed, which comprises: finding out one or more corresponding log data based on a search keyword; determining a desired timestamp from the log data, and regarding the log data containing the timestamp as target data; searching a semantic file for related semantic data based on the search keyword, and finding out related log data based on the related semantic data; time filtering the related log data to obtain filtered log data; establishing a coordinate system by mapping the target data and the filtered log data onto mapping points of the coordinate system; semantically linking the filtered log data, and dying the filtered log data and the target data; and counting the number of lines related to the target data and the filtered log data, and generating links thereto.

In an embodiment of the present invention, determining a desired timestamp from the log data comprises selecting log data containing the timestamp from a plurality of corresponding log data, or obtaining the timestamp according to a preset time period.

In an embodiment of the present invention, the semantic file is an XML semantic file or other structured data files which define semantic data related to the search keyword.

In an embodiment of the present invention, time filtering the related log data to obtain filtered log data comprises time filtering the related log data based on the timestamp.

In an embodiment of the present invention, the related log data within a time period around the timestamp is selected as the filtered log data.

According to an embodiment of the present invention, establishing a coordinate system by mapping the target data and the filtered log data onto mapping points of the coordinate system comprises: establishing an X-axis representing time and Y-axis representing processing steps; and mapping the target data and the filtered log data onto mapping points in the coordinate system according to corresponding time information and processing step information.

According to an embodiment of the present invention, some of the mapping points are connected to form a waveform.

According to an embodiment of the present invention, semantically linking the filtered log data, and dying the filtered log data and the target data comprise: determining semantic closeness between the filtered log data and the search keyword, the semantic closeness being determined based on the level of conversion to show semantic relevance.

According to an embodiment of the present invention, the target data is dyed red, system logs dyed blue; log data having semantic relevance of Level One dyed yellow, and the rest log data gray.

Counting the number of lines related to the target data and the filtered log data, and generating links thereto comprise counting the number of log data related to the keyword and the related semantic data, and generating links to said log data.

According to an embodiment of the present invention, the proposed method further comprises displaying, at the mapping points, the number of corresponding related lines According to an embodiment of the present invention, a device for searching and displaying scattered logs is proposed, which comprises: a log searching component for finding out one or more corresponding log data based on a search keyword; a timestamp determining component for determining a desired timestamp from the log data, and regarding the log data containing the timestamp as target data; a related semantic data searching component for searching a semantic file for related semantic data based on the search keyword, and finding out related log data based on the related semantic data; a filtering component for time filtering the related log data to obtain filtered log data; a mapping component for establishing a coordinate system by mapping the target data and the filtered log data onto mapping points of the coordinate system; a dye component for semantically linking the filtered log data, and dying the filtered log data and the target data; and a counting component for counting the number of lines related to the target data and the filtered log data, and generating links thereto.

In an embodiment of the present invention, the timestamp determining component selects log data containing the desired timestamp from a plurality of corresponding log data, or obtains the desired timestamp according to a preset time period.

In an embodiment of the present invention, the filtering component time filters the related log data based on the timestamp.

In embodiment of the present invention, the filtering component selects the related log data within a time period around the timestamp as the filtered log data.

In an embodiment of the present invention, the mapping component establishes an X-axis representing time and Y-axis representing processing steps; and maps the target data and the filtered log data onto mapping points in the coordinate system according to corresponding time information and processing step information.

In an embodiment of the present invention, the mapping component connects some of the mapping points to form a waveform.

According to an embodiment of the present invention, the dye component determines semantic closeness between the filtered log data and the search keyword based on the level of conversion to show semantic relevance.

According to an embodiment of the present invention, the dye component dyes the target data red, system logs blue; log data having semantic relevance of Level One yellow, and the rest log data gray.

In an embodiment of the present invention, the counting component counts the number of log data related to the keyword and the related semantic data, and generates links to said log data.

In an embodiment of the present invention, the counting component further displays, at the mapping points, the number of corresponding related lines.

The method and device proposed in the present invention conduct searches based on semantic of the imaging chain, and presents logs and relationship among the logs in a simple coordinate system, thereby reducing the work load on an engineer and increasing efficiency in troubleshooting. Besides, the present invention makes it possible to get knowledge of physicians' habits in using a product and to optimize workflow of the product.

DETAILED DESCRIPTION OF THE INVENTION

The present invention will be more apparent from the following detailed description of the embodiments by reference to the drawings. Apparently, these embodiments are not exhaustive. Other embodiments, which the ordinary skilled artisan derive from the given embodiments without exercising inventive skills, also fall into the scope of the present invention.

Figure 1:
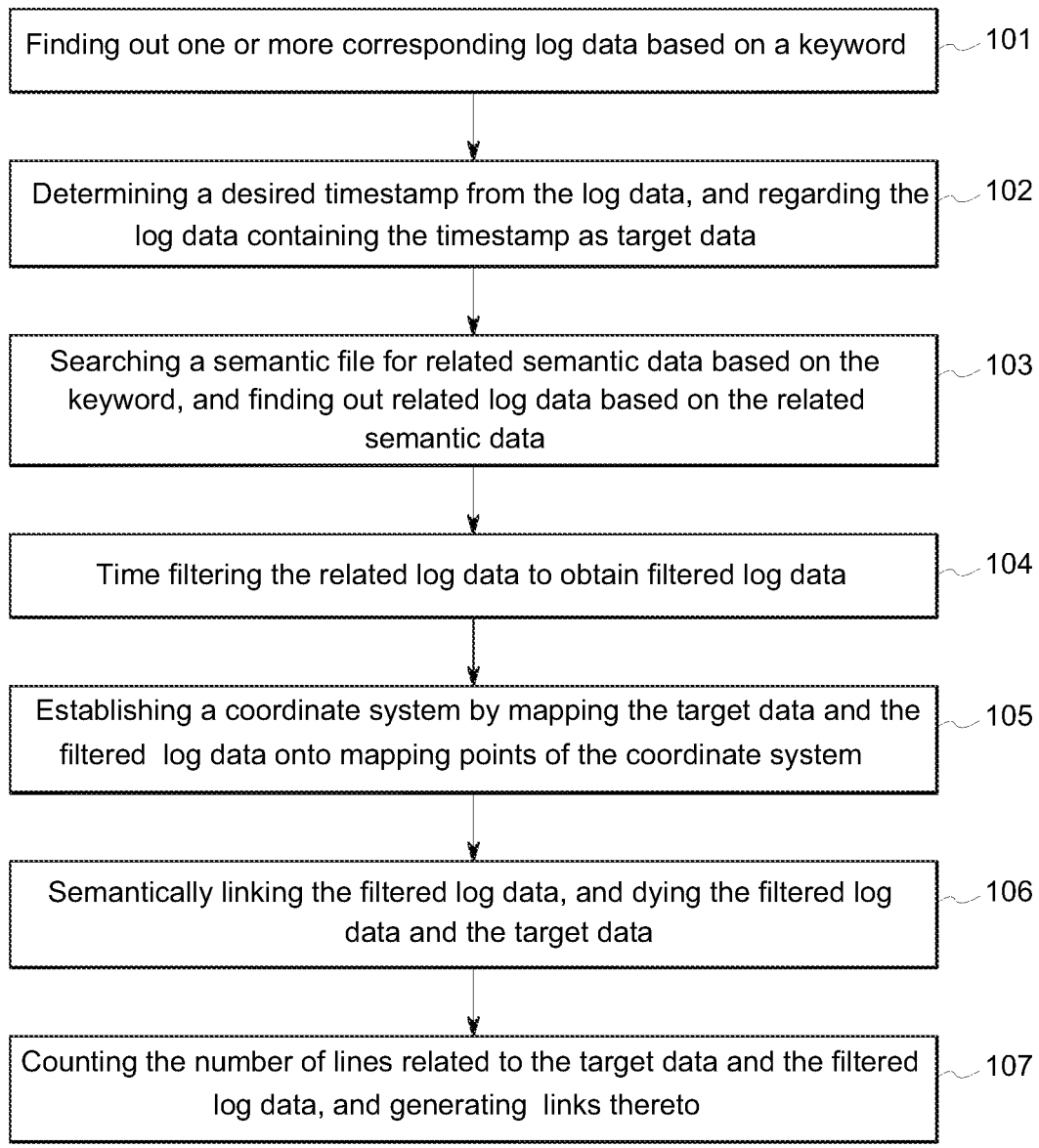
FIG. 1 is a flow chart of a method for searching and displaying scattered logs according to the present invention.

FIG. 1 is a flow chart of a method for searching and displaying scattered logs according to the present invention. Tasks of respective subsystems of a medical imaging device are recorded in log files, which are scattered among these subsystems. Therefore, the medical imaging device knows from which directories to read the log files of these subsystems, and from which to read log files of external systems. The log files of external systems refer to log files of those general systems for supporting the medical imaging device (for example, LINUS system, computer hardware units, etc.).

At Step 101, a keyword is inputted to find out one or more corresponding log data. According to one embodiment of the present invention, a user inputs a search keyword through a user interface. Based on the search keyword, the system finds out, from relevant directories, one or more log data that is directly related to the keyword. In an embodiment, the search keyword may instead be preset in a file, and automatically runs in the case of a system event, for example, shutdown of the system.

At step 102, a desired timestamp is determined from the log data, and the log data containing the desired timestamp is considered as target data. In other words, the log data, which is directly semantically linked and moreover falls within the desired time domain, is selected out of the log data, and regarded as target data. The target data refers to the log data in a log that is directly linked to the search keyword, rather than those which are only related upon conversion. For example, when a user inputs the keyword "shutdown", there must be one or more log data in the log files which completely matches with this keyword. This completely matching log data is referred to as target data. According to one embodiment of the present invention, the system may present the one or more corresponding log data, and the user then clicks to select the log that contains the desired timestamp. For example, if the system finds three items of log data that completely matches, which are generated at the time of 11:11:11 Jun. 10, 2012, 11:11:11 Aug. 10, 2012, and 11:11:11 Oct. 10, 2012 respectively, and if a user wishes to view the latest log data, the user may click the log data with the timestamp of 11:11:11 Oct. 10, 2012. According to an embodiment, a desired timestamp is obtained according to a preset time domain. For example, a user may input a time period while inputting the keyword, for example, from 1 o'clock to 12 o' clock on Oct. 10, 2012. The system will automatically select, out of a plurality of log data, the one within the inputted time period, i.e., the log data that contains the timestamp of 11:11:11 Oct. 10, 2012, and obtains the desired timestamp from the log data. The system then regards the log data with the desired timestamp as the target data.

At Step 103, a semantic file is searched for related semantic data according to the keyword, and then from the related semantic data, related log data is found out.

For a medical imaging device, its main goal is make examinations one by one successfully. These examinations are interrelated with one another. In the present invention, semantics of completing an examination are defined as a semantic unit on an imaging chain, such that the logs that are scattered among various subsystems are organized according to their meanings Thereby, a flow of steps for the examination may be specifically determined, facilitating quantitive and qualitative analysis on each single examination. A single examination is taken as a unit in the present invention and compared with the other examinations along a time axis or a processing step axis, such that the workflow is more direct and apparent. The semantics of an examination are distributed among every subsystem as a series of logs.

The present invention employs a semantic file, which defines semantic data that relates to the search keyword. In one embodiment, the semantic file includes, but is not limited to, an XML semantic file or other structured data files. For example, semantics data that relates to the keyword "shutdown" includes {"tgp error", "Scout Fail" and "ifconfig"}. By taking "tgp error", "Scout Fail", and "ifconfig" as new keywords, the log file is further searched for related log data. Therefore, based on the keyword and the related semantic data, the user may conveniently identify direct subsystems that may relate to the problem, and compare them with semantically related systems, and eventually show systematic information (rather than discrete and incomplete information) on a single map.

The related log data is time filtered at Step 104 to obtain the filtered log data. As a large amount of related log data may be acquired at Step 103, there is a need to filter this large amount of data based on time. According to one embodiment of the present invention, the related log data is filtered based on the desired timestamp. In particular, based on the timestamp determined at Step 102, the related log data that is within a time period around that timestamp is selected as the desired, filtered log data. For example, if Step 102 determines 11:11:11 Oct. 10, 2012 as the desired timestamp, the related log data within 5 hours around the timestamp is selected, that is, the filtered log data falls within the time period between 6:11:11 Oct. 10, 2012 and 11:11:11 Oct. 10, 2012. The particular duration of the time period (for example, five hours as mentioned above) may be preset by the system or inputted by the user. In an embodiment of the present invention, the user may input a time period when inputting a search keyword, for example, from 1 o'clock to 15 o'clock, Oct. 10, 2012. Based on the inputted time period, the system automatically selects, out of the related log data, those that contains the inputted time period.

Subsequently, a coordinate system is established at Step 105, with the target data and the filtered log data being mapped onto the corresponding points of the coordinate system.

According to one embodiment of the present invention, the establishment of the coordinate system comprises setting up an X-axis representing time, and a Y-axis representing processing steps. Take the time period at Step 104 as an example. The origin of the X-axis may be set to 6:11:11 Oct. 10, 2012, and the X-axis comprises the time period between 6:11:11 Oct. 10, 2012 and 16:11:11 Oct. 10, 2012. Persons skilled in the art would appreciate that the origin of the X-axis may be set to 0, and the time period between 6:11:11 Oct. 10, 2012 and 16:11:11 Oct. 10, 2012 may be represented by a numerical number. For example, the number "1" denotes one hour, and numbers "0" through "9" are used on the X-axis to represent the time period between 6:11:11 Oct. 10, 2012 and 16:11:11 Oct. 10, 2012. The present invention is not limited to any particular presentations of the time periods.

An examination with a medical imaging device involves a plurality of subsystems, which may be responsible for respective processing steps. For example, subsystem A conducts Step 1; subsystem B Step 2; and subsystem C Step 3. The Y-axis is established to represent these processing steps. The filtered log data comprises system logs and logs of various subsystems of the medical imaging device. As both the target data and the subsystem logs contain time information and both of them are created by corresponding subsystems, they may be mapped onto the corresponding points of the coordinate system based on their respective time information and processing steps. The system logs may be mapped onto respective points of the coordinate system according to the time information. In one embodiment of the present invention, the coordinate points in the coordinate system onto which the target data and the filtered log data are mapped may be represented by circles. In an embodiment, they may be represented by a rectangle, or a diamond, etc. The embodiments of the present invention are not limited to any particular shapes.

According to an embodiment of the present invention, after mapping the target data and the subsystem logs to the coordinate system, the plurality of mapping points may be connected to generate a waveform for ease of the user's view. Since a plurality of examinations may be done in a particular time period around the desired timestamp, one examination, i.e., one semantic unit, is regarded as a unit of the waveform. The time points at which each examination (one waveform) begins and ends may be read from the log file, and shown on the time X-axis. The mapping points within the waveform may be connected with one another by a dotted line and a solid line. As shown in the waveform, the solid line is used to horizontally connect the log data, which is generated by the subsystems conducting corresponding processes. According to an embodiment, these mapping points may be connected into a different shape for the sake of view by the user, and some auxiliary lines may be additionally used to connect these mapping points. What particular shapes are used should not be construed as a limitation to the present invention.

According to an embodiment, the system logs may be shown, if deemed necessary. For example, if necessary, a user may choose, over the user interface, whether to show the system logs. In the present invention, when the system logs are displayed, they are not shown in the waveform, but in the exterior to the waveform such that the relationship between the primary section and the secondary section of the system is instantly clear.

At Step 106, the filtered log data is linked in terms of semantics, and then dyed together with the target data. In the present invention, it is determined as to how closely the semantic of the filtered log data is related to the search keyword. In particular, this closeness in semantic is evaluated by determining the level of conversion to show semantic relevance. For example, if the keyword is "shutdown", the related semantic may include { "tgp error", "Scout Fail", "ifconfig"}, etc, among which "tgp error" is fatal to the system. If "tgp error" occurs, it may cause the system to directly shut down. In this case, "tgp error" is considered to represent top semantic relevance, i.e., Level One, and the corresponding log is dyed "yellow". As to "ifconfig", there is chance that it may result in "shutdown", but that is dependent on whether it has impact on the key setting "Dataacq" on the semantic chain. If it does have impact, a further decision needs to be made as to whether "Scout" is affected. In this case, although "ifconfig" is related to "shutdown", the semantic relevance is shown only upon three levels of conversion, i.e., semantic relevance of Level Three. In this case, a gray color may be used instead to denote a relatively less semantic closeness. In one embodiment of the present invention, the target data is dyed "red" while the system log data dyed "blue". The log data having semantic relevance of Level One is dyed yellow, and the rest gray. In an embodiment, the target data is dyed red, while the system log data blue. The log data having semantic relevance of Level One is dyed yellow, while the rest levels (Level Two through Level Six generally) are dyed respective colors (which may be set). The other log data that is not semantically related but falls within the same time period is dyed grey. The aforesaid colors are only illustrated to differentiate different log data, and it would be appreciated that different colors may be used. That is, what particular colors are used should not be considered to limit the present invention.

Then, Step 107 counters the number of lines related to the target data and the filtered log data, and generates links thereto. The number of related lines refers to the log data that is related to the search keyword. The present invention counts the number of log data that is related to the keyword and to the related semantic data, and generates links to these log data. Consequently, when the user clicks the mapping points, the user will be given links to these log data, which is then presented before the user. According to one embodiment of the present invention, the number of related lines may be shown at respective mapping points for ease of the user's view. When the user clicks the mapping points, the user will be given links to these log data, which is then presented before the user. What is also shown is what the user has done to create these log data, such that the user may conveniently view and analyze the log data.

According to an embodiment of the present invention, beside all of the mapping points are shown the number of respective related lines. In an embodiment of the present invention, the number of related lines is indicated only beside the mapping points that correspond to the system log data only, or only beside the log data having semantic relevance of Level One. Persons skilled in the art would be able to choose and configure the elements to be shown on the user interface according to circumstance.

Figure 2:
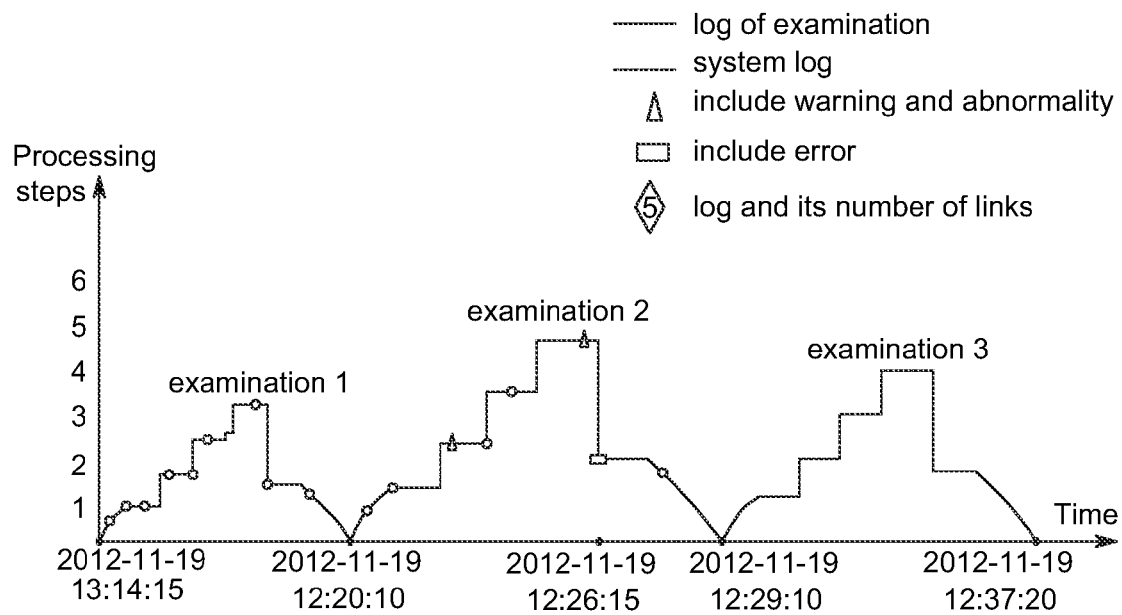
FIG. 2 is a user interface displaying examination log data acquired using the method as shown in FIG. 1.

FIG. 2 shows a user interface that shows examination log data obtained according to the method as shown in FIG. 1. As shown in FIG. 2, an examination is defined as a semantic unit. There are in total three examination semantic sequences. The red circle (i.e., the target data) represents an error containing log, while the yellow circle (i.e., the log data having semantic relevance of Level One) indicates a log that contains warning or abnormality. FIG. 2 does not show system log or the number of related lines beside the log data.

Figure 3:
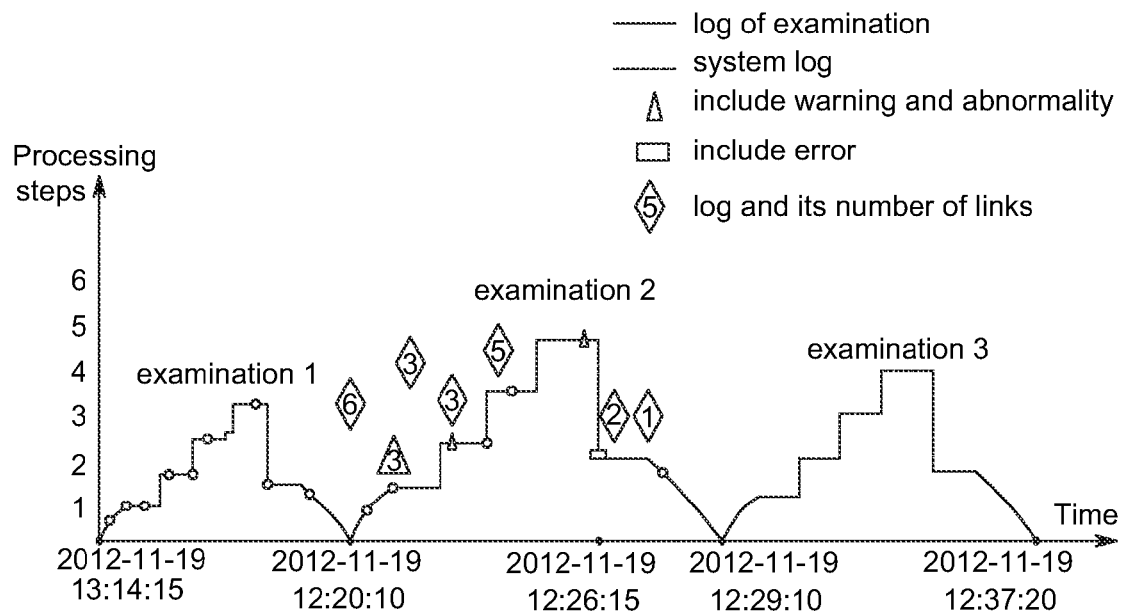
FIG. 3 is a user interface displaying examination log data and system log data acquired using the method as shown in FIG. 1.

FIG. 3 illustrates a user interface showing examination log data and system log data obtained using the method as shown in FIG. 1. As compared with FIG. 2, FIG. 3 additionally shows system log with a blue circle as well as the number of lines related to the system log.

Figure 4:
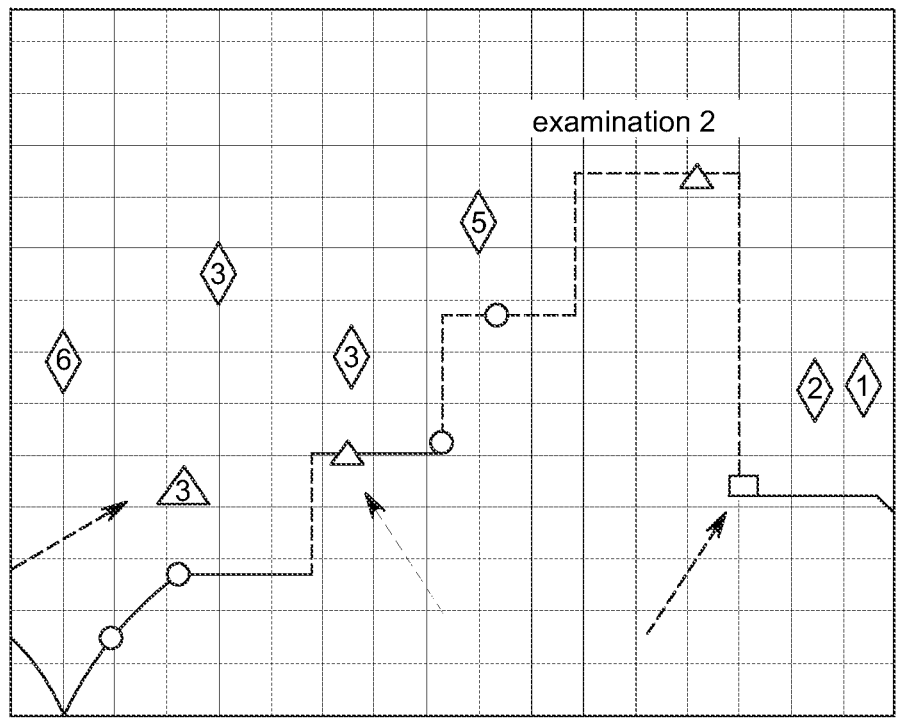
FIG. 4 is a diagram for troubleshooting.
Figure 5:
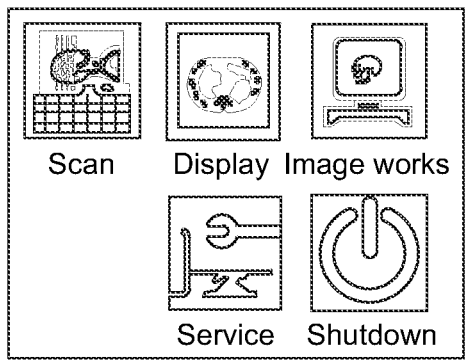
FIG. 5 shows information related to the troubleshooting as shown in FIG. 4.

The embodiments employed in the present invention are able to quickly analyze the log files for troubleshooting. As shown in FIG. 3, shown around the error containing log are in total three logs that contain warning or abnormality. By clicking these logs the user may be able to identify the trouble. FIG. 4 illustrates an example of troubleshooting. As is shown, by clicking the system log accompanied by the number "3", the system provides a link to the system log, and shows what the user has done to create these system logs. FIG. 5 shows these system logs, and presents before the user what has been done to generate these system logs.

In view of the above, the method proposed in the present invention conducts search based on the semantic of an imaging chain, and displays the logs and relationship therebetween in a simple coordinate system. As a result, engineers are able to quickly analyze the logs for troubleshooting, which thereby increase the efficiency in troubleshooting and reduce the workload of the engineers.

Additionally, the present invention makes it possible that an engineer may have knowledge of how a physician uses a medical imaging device by viewing an examination waveform, which may optimize the workflow of a product. In the present invention, a medical imaging device may scan a head of a human being. When the engineer inputs a keyword such as "head scan", the waveforms of a series of head scan examinations around a certain time point may be generated. The time it takes to complete an examination should be the same, i.e., the length of time shown in the waveform should be the same. If a waveform has a time length that is obviously different from the other examinations, the logs may be viewed to examine the physician's operational habit, which can optimize the workflow of a product. In addition, in this embodiment, if a waveform has a time length that is obviously different from the other examinations, the engineer may reasonably assume that the scan at issue runs potential risks or problems, and may view the logs to locate these potential problems and determine appropriate solutions quickly.

Given the foregoing disclosure of the present invention, persons skilled in the art would appreciate that the present invention is suited for searching and displaying log data within a plurality of time periods. In accordance with one embodiment of the present invention, a user may input a plurality of time periods when inputting a keyword, or select a plurality of desired timestamps, or both. After selecting related log data within a plurality of time periods, the plurality of time periods may be established along the positive direction of the X-axis. Subsequently, the target data and the filtered log data are mapped to the coordinate system within these time periods, such that the semantic waveforms within different time periods according to the same keyword may be displayed in the same coordinate system, facilitating the view and comparison of the engineers.

In view of the foregoing descriptions, persons skilled in the art would understand that the present invention is additionally suited for a search using a plurality of keywords. In an embodiment of the present invention, the user may input a plurality of keywords through the user interface, and find out a plurality of corresponding log data based on the plurality of keywords. A plurality of desired timestamps is determined from the log data, and the log data containing these timestamps is regarded as target data. Accordingly, related semantic data is located from semantic files based on the plurality of keywords, which data is then used to find out related log data. The related log data is time filtered to obtain the filtered log data. Thereafter, a coordinate system is established by mapping the plurality of target data and the filtered log data onto the mapping points in the coordinate system. In particular, a plurality of time periods may be indicated along the positive direction of the X-axis to correspond to the plurality of target data. Then the plurality of target data and filtered log data are mapped to the proper time periods. The filtered log data are linked based on semantics, and then dyed together with the target data. Finally, the number of lines related to the target data and the filtered log data is counted, and proper links are generated. By using the foregoing method, a semantic waveform related to a plurality of keywords may be shown in the same coordinate system to better meet the user's needs. The aforesaid establishing a plurality of time periods along the positive direction of the X-axis is illustrated as an example only. That is, these time periods may be also established along the negative direction of the X-axis, and it only needs to distinguish between these time periods. This should not be construed as a limitation to the present invention.

Figure 6:
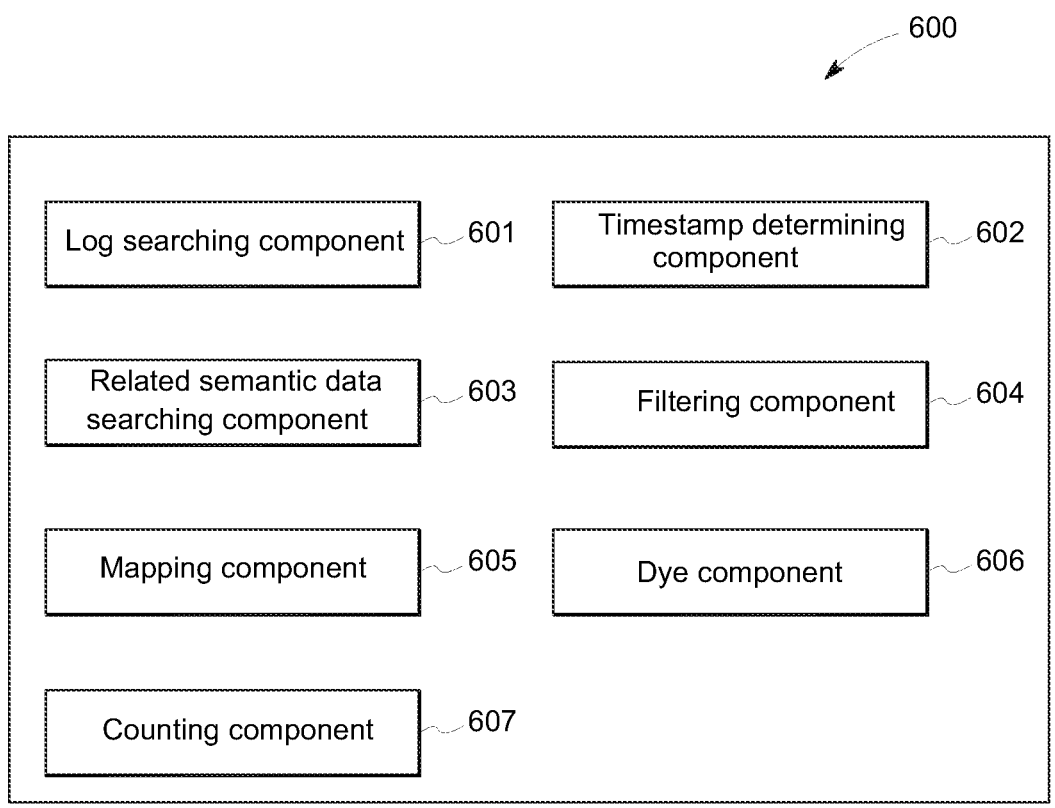
FIG. 6 illustrates a device for searching and displaying scattered logs according to the present invention.

FIG. 6 illustrates a device 600 for searching and displaying scattered logs. Device 600 comprises: a log searching component 601 for searching one or more corresponding log data based on a keyword; a timestamp determining component 602 for obtaining a desired timestamp from the log data, and regarding the log data containing the timestamp as target data; a related semantic data searching component 603 for searching a semantic file for related semantic data based on the keyword, and finding out related log data according to the related semantic data; a filtering component 604 for time filtering the related log data to obtain filtered log data; a mapping component 605 for establishing a coordinate system by mapping the target data and the filtered log data onto corresponding mapping points in the coordinate system; a dye component 606 for semantically linking the filtered log data and dying the filtered log data and target data; and a counting component 607 for counting lines related to the target data and the filtered log data and generating links thereto. The semantic file may be an XML semantic file or other structured data files, which defines semantic data related to the keyword.

The timestamp determining component selects the log data containing a desired timestamp from a plurality of corresponding log data, or determines a desired timestamp according to a preset time period. The filtering component time filters the related log data based on the determined timestamp. In particular, the filtering component selects the related log data that falls within a time period around the desired timestamp as the filtered log data. The mapping component establishes an X-axis denoting time and a Y-axis denoting processing steps, and maps the target data and the filtered log data onto the corresponding mapping points in the coordinate system based on respective time information and processing steps. The mapping component connects some of the mapping points to generate a waveform. The dye component determines the semantic closeness between the filtered log data and the keyword based on the level of conversion to show semantic relevance. Thereafter, the dye component dyes the target data red while the system log blue, the log data having semantic relevance of Level One red, while the rest gray. The counting component determines the number of log data that is related to the keyword and the semantic data thereof, and generates links to these log data. The counting component also displays the number of related lines at the corresponding mapped points.

The methods proposed in the present invention may be implemented by hardware, software, and firmware or any combinations thereof. The aforesaid embodiments of the present invention are illustrative only, and should not be construed to limit the scope of the present invention. Any equivalent alterations to the structure or workflow made based on the description and the figures of the present invention, or any direct or indirect applications of the present invention to other relevant technical fields are also considered to fall into the scope of the present invention.

What is claimed is:

1. A method for searching and displaying data from scattered logs of a medical imaging device and a set of subsystems thereof, the method comprising:
    identifying log data from the medical imaging device and the set of subsystems based on a keyword;
    selecting a timestamp, and in response to the selecting, providing target data associated with the timestamp, wherein the target data is included in the log data;
    searching a set of semantic files, each semantic file from the set of semantic files being associated with a corresponding subsystem of the set of subsystems for related semantic data based on the keyword, and finding out related log data based on the related semantic data;
    time filtering the related log data to obtain filtered log data, the filtered log data comprising at least one system log and a subsystem log from the medical imaging device;
    establishing a coordinate system by mapping the target data and the filtered log data onto mapping points of the coordinate system;
    semantically linking the filtered log data, and dying the filtered log data and the target data; and
    counting the number of lines related to the target data and the filtered log data, and generating links thereto, and wherein
    the step of mapping comprises:
    establishing an X-axis representing time and a Y-axis representing process steps, and
    mapping the target data and the filtered log data onto mapping points of the coordinate system according to corresponding time information and processing step information.

2. The method according to claim 1, wherein selecting the timestamp includes obtaining the timestamp according to a preset time period.

3. The method according to claim 1, wherein a semantic file from the set of semantic files is an XML semantic file or other structured data files which define semantic data related to the keyword.

4. The method according to claim 1, wherein time filtering the related log data includes time filtering the related log data based on the timestamp.

5. The method according to claim 4, further comprising:
    selecting the related log data within a time period around the timestamp as the filtered log data.

6. The method according to claim 1, wherein some of the mapping points are connected to form a waveform.

7. The method according to claim 1, wherein semantically linking the filtered log data and dying the filtered log data and the target data comprise:
    determining semantic closeness between the filtered log data and the keyword, the semantic closeness being determined based on the level of conversion.

8. The method according to claim 7, wherein the target data is dyed red, system logs dyed blue, log data having semantic relevance of Level One dyed yellow, and the rest log data dyed gray.

9. The method according to claim 1, wherein the counting the number of lines related to the target data and the filtered log data, and generating links thereto comprise:
    counting the number of log data related to the keyword and the related semantic data, and generating links to the log data.

10. The method according to claim 9, further comprising: displaying, at the mapping points, the number of corresponding related lines.

11. A system for searching and displaying data from scattered logs of a medical imaging device and a set of subsystems thereof, the system comprising:
    a log searching component configured to determine log data from the medical imaging device and the set of subsystems based on a keyword;
    a timestamp determining component configured to select a timestamp, and in response to selecting the timestamp, provide target data associated with the timestamp, wherein the target data is included in the log data;

a related semantic data searching component configured to search a set of semantic files, each semantic file from the set of semantic files being associated with a corresponding subsystem of the set of subsystems, for related semantic data based on the keyword, and to find related log data based on the related semantic data;

a filtering component for time filtering the related log data to obtain filtered log data, the filtered log data comprising at least one system log and a subsystem log from the medical imaging system;

a mapping component for establishing a coordinate system by mapping the target data and the filtered log data onto mapping points of the coordinate system, the mapping including establishing an X-axis representing time and a Y-axis representing process steps, and mapping the target data and the filtered log data onto the mapping points according to corresponding time information and processing step information of the examination;

a dye component for semantically linking the filtered log data, and dying the filtered log data and the target data; and a counting component for counting the number of lines related to the target data and the filtered log data, and generating links thereto.

12. The system according to claim 11, wherein the timestamp determining component selects obtains the timestamp according to a preset time period.

13. The system according to claim 11, wherein a semantic file from the set of semantic files is an XML semantic file or other structured data files which define semantic data related to the keyword.

14. The system according to claim 11, wherein the filtering component time filters the related log data based on the timestamp.

15. The system according to claim 14, wherein the filtering component selects the related log data within a time period around the timestamp as the filtered log data.

16. The system according to claim 11, wherein the mapping component connects some of the mapping points to form a waveform.

17. The system according to claim 11, wherein the dye component determines semantic closeness between the filtered log data and the keyword, the semantic closeness being determined based on the level of conversion to show semantic relevance.

18. The system according to claim 17, wherein the dye component dyes the target data red, system logs blue, log data having semantic relevance of Level One yellow, and the rest log data gray.

19. The system according to claim 11, wherein the counting component counts the number of log data related to the keyword and the related semantic data, and generates links to the log data.

20. The system according to claim 19, wherein the counting component further displays, at the mapping points, the number of corresponding related lines.

* * * * *